US009895559B2

United States Patent
Chang et al.

(10) Patent No.: US 9,895,559 B2
(45) Date of Patent: *Feb. 20, 2018

(54) ROBOT

(71) Applicant: Daegu Gyeongbuk Institute of Science and Technology, Daegu (KR)

(72) Inventors: Pyung Hun Chang, Seoul (KR); Gezgin Erkin, Izmir (TR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 336 days.

This patent is subject to a terminal disclaimer.

(21) Appl. No.: 14/541,124

(22) Filed: Nov. 13, 2014

(65) Prior Publication Data

US 2015/0283407 A1  Oct. 8, 2015

(30) Foreign Application Priority Data

Apr. 7, 2014  (KR) .................. 10-2014-0041386

(51) Int. Cl.
| | |
|---|---|
| *A61N 5/10* | (2006.01) |
| *A61B 6/00* | (2006.01) |
| *A61B 34/30* | (2016.01) |
| *B25J 18/00* | (2006.01) |
| *B25J 9/16* | (2006.01) |
| *A61B 34/35* | (2016.01) |
| *A61B 34/00* | (2016.01) |
| *B25J 9/02* | (2006.01) |

(52) U.S. Cl.
CPC .......... *A61N 5/1083* (2013.01); *A61B 6/4007* (2013.01); *A61B 6/44* (2013.01); *A61B 6/4458* (2013.01); *A61B 34/30* (2016.02); *A61B 34/35* (2016.02); *A61B 34/77* (2016.02); *A61N 5/1084* (2013.01); *B25J 9/02* (2013.01); *B25J 9/1666* (2013.01); *B25J 18/005* (2013.01); *A61B 2034/305* (2016.02); *G05B 2219/39096* (2013.01); *Y10S 901/23* (2013.01); *Y10T 74/20317* (2015.01)

(58) Field of Classification Search
CPC .. A61N 5/1083; A61N 5/1084; A61B 6/4007; A61B 6/44; A61B 6/4458
USPC ................. 378/9, 65, 68, 196, 197
See application file for complete search history.

(56) References Cited

U.S. PATENT DOCUMENTS

| | | | | |
|---|---|---|---|---|
| 4,894,855 A | * | 1/1990 | Kresse | A61B 6/032 378/189 |
| 5,078,140 A | * | 1/1992 | Kwoh | A61B 34/30 378/20 |

(Continued)

FOREIGN PATENT DOCUMENTS

| | | |
|---|---|---|
| CN | 101304701 A | 11/2008 |
| EP | 1 384 493 A1 | 1/2004 |

(Continued)

OTHER PUBLICATIONS

International Search Report for International application No. PCT/KR2014/010950, dated Dec. 23, 2014.
Extended European Search Report for European Patent Application No. 14866812.2, dated Aug. 10, 2016.
Office Action for Chinese Patent Application No. 20148002006.0, dated Jul. 14, 2016.

(Continued)

*Primary Examiner* — Allen C. Ho

(57) ABSTRACT

A robot includes a link portion including a plurality of link members and a drive portion to rotate the link members, and axes of rotation of the drive portion extending from end portions of the link members is positioned at an identical point.

17 Claims, 6 Drawing Sheets

(56) References Cited

U.S. PATENT DOCUMENTS

| | | | | |
|---|---|---|---|---|
| 5,635,721 A * | 6/1997 | Bardi | ............... | A61N 5/01 250/492.3 |
| 6,200,024 B1 * | 3/2001 | Negrelli | ............... | A61B 6/4233 378/196 |
| 6,338,714 B1 * | 1/2002 | Krause | ............... | A61G 12/004 128/897 |
| 6,435,715 B1 * | 8/2002 | Betz | ............... | A61B 6/4458 378/197 |
| 6,530,688 B1 * | 3/2003 | Muller | ............... | B25J 17/0266 378/197 |
| 6,590,958 B2 * | 7/2003 | Barber | ............... | A61B 6/107 378/196 |
| 6,592,259 B2 * | 7/2003 | Crain | ............... | A61B 6/107 378/196 |
| 6,826,254 B2 * | 11/2004 | Mihara | ............... | A61N 5/10 250/492.3 |
| 6,869,217 B2 * | 3/2005 | Rasche | ............... | A61B 6/4441 378/193 |
| 6,977,987 B2 * | 12/2005 | Yamashita | ............... | A61N 5/10 378/64 |
| 7,081,700 B2 * | 7/2006 | Okumura | ............... | B25J 7/00 310/323.17 |
| 7,085,347 B2 * | 8/2006 | Mihara | ............... | A61N 5/10 378/197 |
| 7,188,999 B2 * | 3/2007 | Mihara | ............... | A61N 5/10 378/17 |
| 7,239,684 B2 * | 7/2007 | Hara | ............... | A61N 5/1049 378/65 |
| 7,266,176 B2 * | 9/2007 | Allison | ............... | A61N 5/1031 378/205 |
| 7,401,977 B2 * | 7/2008 | Graumann | ............... | A61B 6/4441 378/197 |
| 7,441,953 B2 * | 10/2008 | Banks | ............... | A61B 5/1038 378/197 |
| 7,500,784 B2 * | 3/2009 | Grebner | ............... | A61B 6/4441 378/193 |
| 7,505,559 B2 * | 3/2009 | Kuduvalli | ............... | A61N 5/1049 378/205 |
| 7,530,739 B2 * | 5/2009 | Lurz | ............... | A61B 6/4441 378/197 |
| 7,590,219 B2 * | 9/2009 | Maurer, Jr. | ............... | A61N 5/103 378/145 |
| 7,620,144 B2 * | 11/2009 | Bodduluri | ............... | A61B 6/02 378/41 |
| 7,623,623 B2 * | 11/2009 | Raanes | ............... | A61N 5/1049 378/205 |
| 7,693,257 B2 * | 4/2010 | Allison | ............... | A61N 5/103 378/108 |
| 7,720,196 B2 * | 5/2010 | Zhang | ............... | A61B 5/113 378/65 |
| 7,724,870 B2 * | 5/2010 | Maltz | ............... | A61B 6/025 378/197 |
| 7,891,935 B2 * | 2/2011 | Kremerman | ............... | B25J 9/042 414/744.5 |
| 7,894,649 B2 * | 2/2011 | Fu | ............... | A61N 5/1049 378/65 |
| 7,905,658 B2 * | 3/2011 | Groβ | ............... | 378/193 |
| 7,934,869 B2 * | 5/2011 | Ivanov | ............... | A61N 5/1049 378/20 |
| 7,938,579 B2 * | 5/2011 | Groβ | ............... | A61B 6/4458 378/197 |
| 7,972,061 B2 * | 7/2011 | Groβ | ............... | A61B 6/4441 378/197 |
| 7,978,817 B2 * | 7/2011 | Rietzel | ............... | A61N 5/1049 378/197 |
| 7,985,023 B2 * | 7/2011 | Groβ | ............... | A61B 6/4441 378/197 |
| 7,988,357 B2 * | 8/2011 | Hornung | ............... | A61B 6/4458 378/197 |
| 8,011,828 B2 * | 9/2011 | Beimler | ............... | B25J 9/104 378/189 |
| 8,113,711 B2 * | 2/2012 | Beimler | ............... | B25J 9/104 378/189 |
| 8,126,114 B2 * | 2/2012 | Naylor | ............... | A61N 5/1049 378/65 |
| 8,130,907 B2 * | 3/2012 | Maurer, Jr. | ............... | A61B 6/00 378/65 |
| 8,180,020 B2 * | 5/2012 | Kilby | ............... | A61N 5/1031 378/65 |
| 8,262,554 B2 * | 9/2012 | Sayeh | ............... | A61B 6/032 378/65 |
| 8,295,435 B2 * | 10/2012 | Wang | ............... | A61N 5/10 378/65 |
| 8,303,575 B2 * | 11/2012 | Rodriguez | ............... | A61B 34/70 606/1 |
| 8,315,356 B2 * | 11/2012 | Core | ............... | A61N 5/1049 378/205 |
| 8,320,517 B2 * | 11/2012 | Dennerlein | ............... | A61B 6/032 378/4 |
| 8,459,867 B2 * | 6/2013 | Muller | ............... | A61B 6/4464 378/196 |
| 8,469,945 B2 * | 6/2013 | Schena | ............... | B25J 17/0258 606/1 |
| 8,483,358 B2 * | 7/2013 | Allison | ............... | A61B 6/00 378/65 |
| 8,534,915 B2 * | 9/2013 | Maschke | ............... | A61B 6/4411 378/196 |
| 8,559,596 B2 * | 10/2013 | Thomson | ............... | G06T 7/0014 378/20 |
| 8,611,495 B2 * | 12/2013 | Maschke | ............... | A61B 6/4014 378/197 |
| 8,824,630 B2 * | 9/2014 | Maurer, Jr. | ............... | G06F 19/3481 378/20 |
| 8,849,633 B2 * | 9/2014 | Core | ............... | G06F 19/3437 378/18 |
| 8,944,680 B2 * | 2/2015 | Graumann | ............... | A61B 6/4452 250/491.1 |
| 8,989,846 B2 * | 3/2015 | Kuduvalli | ............... | A61B 6/00 378/181 |
| 9,108,048 B2 * | 8/2015 | Maurer, Jr. | ............... | A61B 6/5247 |
| 9,126,036 B2 * | 9/2015 | Leek | ............... | A61N 5/1077 |
| 9,149,656 B2 * | 10/2015 | Tanabe | ............... | A61N 5/1067 |
| 9,248,571 B2 * | 2/2016 | Amberg | ............... | B25J 9/1664 |
| 9,625,581 B2 * | 4/2017 | Chang | ............... | B29C 67/0085 |
| 2004/0183404 A1 | 9/2004 | Okumura et al. | | |
| 2007/0173977 A1 | 7/2007 | Schena | | |
| 2009/0041565 A1 | 2/2009 | Rodriguez Y Baena | | |

FOREIGN PATENT DOCUMENTS

| | | |
|---|---|---|
| JP | 2002-253687 | 9/2002 |
| JP | 2004-283926 A | 10/2004 |
| JP | 2008-161015 A | 7/2008 |
| JP | 2009-512473 A | 3/2009 |
| KR | 10-1334759 | 8/2008 |
| KR | 2008-0091236 A | 10/2008 |
| KR | 2009038051 | 4/2009 |
| KR | 20100119106 A | 4/2009 |
| KR | 202010000663 U | 6/2010 |
| WO | WO-2007/045810 A2 | 4/2007 |
| WO | WO-2010/044536 A1 | 4/2010 |

OTHER PUBLICATIONS

Search Report for Chinese Patent Application No. 20148002006.0, dated Jul. 14, 2016.

Office Action for Japanese Patent Application No. 2016-512862, dated Jun. 21, 2016.

Office Action cited in KR 10-2014-0041386, dated Apr. 7, 2014.

Office Action issued in Japanese Patent Application No. 2016-512862, dated Nov. 22, 2016.

* cited by examiner

ROBOT

CROSS-REFERENCE TO RELATED APPLICATION

This application claims the benefit of Korean Patent Application No. 10-2014-0041386, filed on Apr. 7, 2014, in the Korean Intellectual Property Office, the disclosure of which is incorporated herein by reference.

BACKGROUND

1. Field of the Invention

Embodiments of the present invention relate to a robot, and more particularly, to a robot that may aim at a target more accurately and rapidly.

2. Description of the Related Art

Radiation therapy is a form of treatment to kill cancer cells using high-energy radiation. Radiation refers to a material mediating propagation or a phenomenon of energy propagating through a space, and an X-ray is a typical example of the radiation.

Radiation therapy is one of the three most prevalent cancer treatments, in company with surgery and chemotherapy. In general, radiation therapy may not require hospitalization, take a few to about 30 minutes per day, and be painless during treatment.

As radiation therapy apparatuses, X-Knife (Radionics, U.S.A.), Novalis Tx (BrainLAB, Germany), Peacok (NOMOS Corp., U.S.A.), Trilogy (Varian Medical System, U.S.A.), and CyberKnife (Accuray Inc., U.S.A.) are known. Many of the radiation therapy apparatuses are evolving to reduce an error occurring during treatment and increase an accuracy based on technology of Image Guided Radiotherapy (IGRT) and a linear accelerator.

CyberKnife is a high-precision stereotactic radiation therapy exclusive apparatus that may intensively irradiate a tumor portion in various directions by providing a small linear accelerator to a robot arm freely moving with six joints.

CyberKnife may provide a precise treatment by tracking coordinates of a gold marker inserted into a body and a skeleton image using real-time image guided technology, without an invasive fixing device. In addition, contrary to Gamma Knife used to treat brain tumors, CyberKnife may be used to treat cancer throughout a human body. Further, CyberKnite may be used for fractionated radiation therapy administered a few times, rather than once.

Recently, varied research is being conducted on CyberKnife. For example, Korean Patent Application No. 2009-0038051, filed on Apr. 30, 2009, discloses "System for radiotherapy planning information viewer".

SUMMARY

An aspect of the present invention provides a robot that may be provided in a compact design to reduce an overall weight.

Another aspect of the present invention also provides a robot that may increase a directivity with respect to a target through easy control.

Still another aspect of the present invention also provides a robot that may aim at a target more accurately and rapidly, thereby reducing a treatment or surgery time.

Yet another aspect of the present invention also provides a robot that may prevent a mutual collision between link members during an operation of a drive portion.

Further another aspect of the present invention also provides a robot including an additional angle adjustment element disposed at an end portion of a second link member or an emitting member to efficiently adjust an angle at which the emitting member faces a target.

According to an aspect of the present invention, there is provided a robot including a link portion comprising a plurality of link members, and a drive portion to rotate the link members. Axes of rotation of the drive portion extending from end portions of the link members may be positioned at an identical point.

The link portion may include a first link member, and a second link member connected to an end portion of the first link member.

The first link member and the second link member may be provided in a form of arcs and disposed on concentric spheres, respectively.

The drive portion may include a first drive member disposed at one end of the first link member to rotate the first link member on a first axis of rotation, and a second drive member disposed at another end of the first link member to rotate the second link member on a second axis of rotation.

An emitting member may be disposed at another end of the second link member to face a target.

According to another aspect of the present invention, there is also provided a robot including a first link member, a first drive member disposed at one end of the first link member to rotate the first link member on a first axis of rotation, a second link member connected to another end of the first link member, a second drive member disposed between the other end of the first link member and one end of the second link member to rotate the second link member on a second axis of rotation, and an emitting member disposed at another end of the second link member. The first axis of rotation and the second axis of rotation may be positioned at an identical location of a target.

The first link member and the second link member may be provided in a form of arcs and disposed on concentric spheres on which the target is centered, respectively.

An angle adjustment element may be disposed at the second link member or the emitting member to adjust an angle at which the emitting member faces the target.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
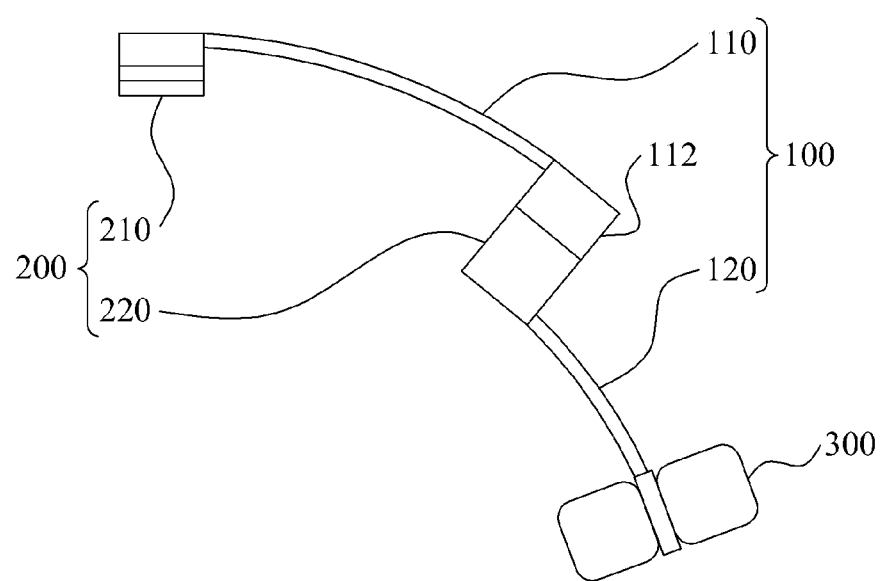
FIG. 1 is a front view illustrating a robot according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

Figure 2:
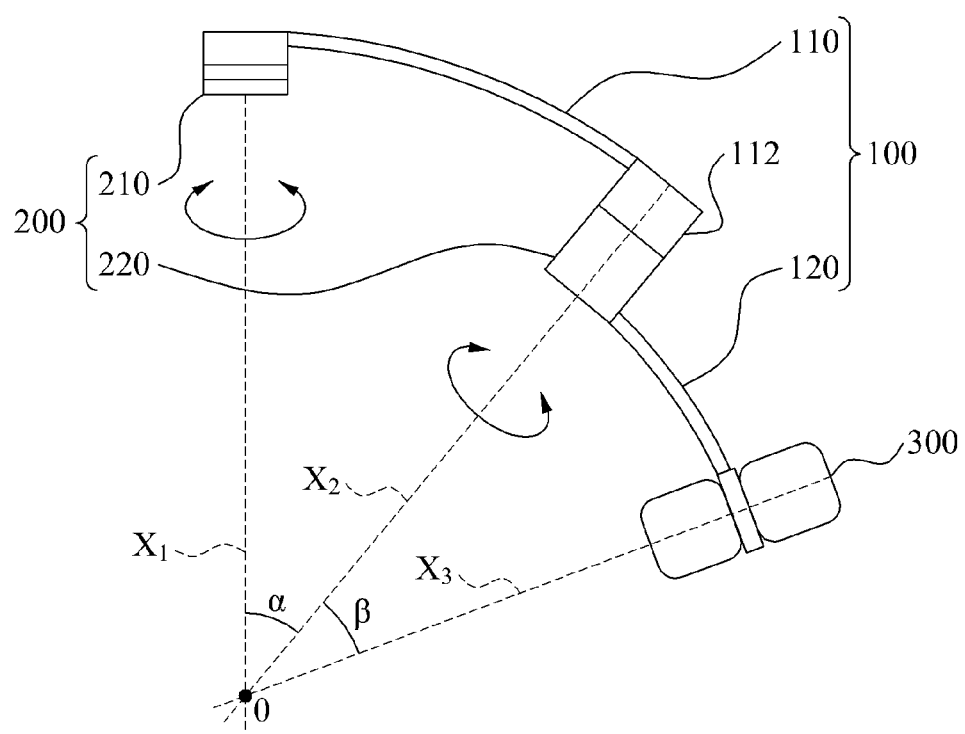
FIG. 2 is a view illustrating axes of rotation being positioned at an identical point in a robot according to an embodiment of the present invention.
Figure 3:
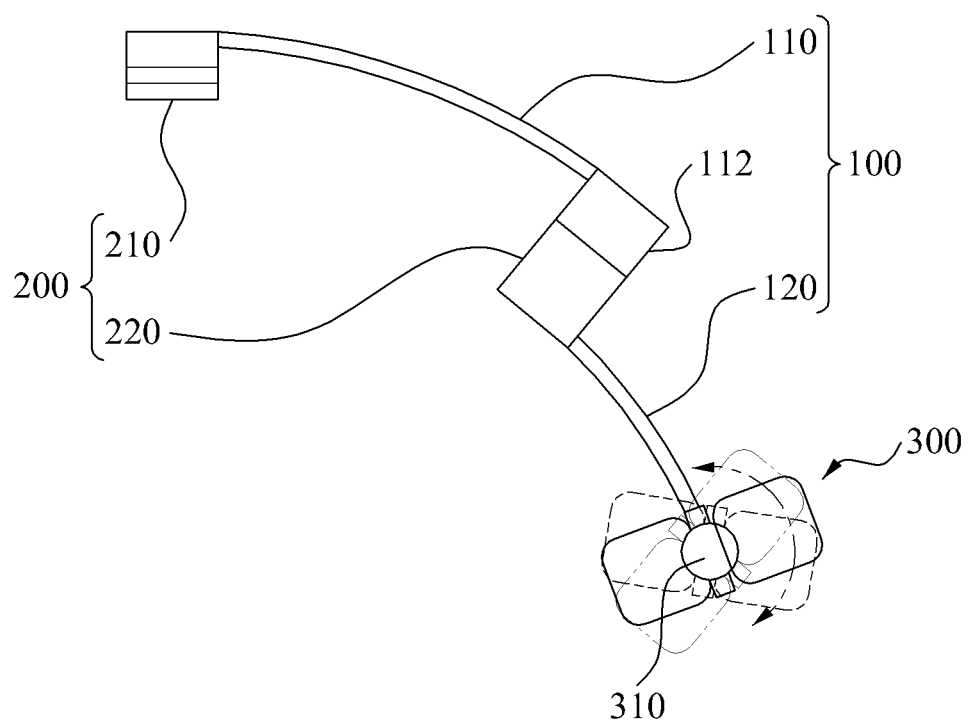
FIG. 3 is a view illustrating an angle adjustment element provided at an emitting member of a robot according to embodiment of the present invention.
Figure 4:
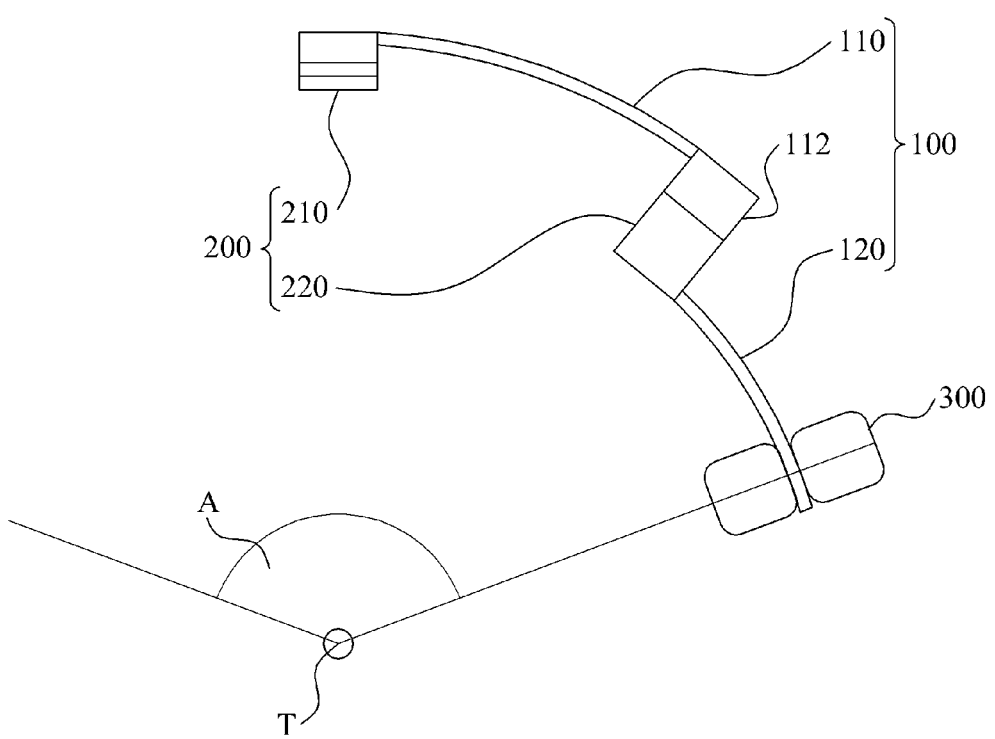
FIG. 4 is a view illustrating a radiation range of an emitting member of a robot according to an embodiment of the present invention.

FIG. 1 is a front view illustrating a robot 10 according to an embodiment of the present invention. FIG. 2 is a view illustrating axes of rotation being positioned at an identical point in the robot 10. FIG. 3 is a view illustrating an angle adjustment element provided at an emitting member 300 of the robot 10. FIG. 4 is a view illustrating a radiation range of the emitting member 300 of the robot 10.

Referring to FIG. 1, the robot 10 may include a link portion 100 and a drive portion 200.

The link portion 100 may include a plurality of link members. The plurality of link members may include a first link member 110 and a second link member 120.

The first link member 110 and the second link member 120 may be connected to each other.

The first link member 110 and the second link member 120 may be connected to each other, with the drive portion 200 disposed therebetween.

The first link member 110 and the second link member 120 may be provided in a form of arcs and disposed on concentric spheres, respectively.

For example, the first link member 110 may correspond to an arc disposed on a large concentric sphere, and the second link member 120 may correspond to an arc disposed on a small concentric sphere. The first link member 110 and the second link member 120 may be disposed away from a location at which the first link member 110 and the second link member 120 are radially spaced from each other.

The first link member 110 and the second link member 120 may be provided in different lengths. For example, the first link member 110 may have a greater length than the second link member 120. Thus, when the second link member 120 rotates inside the first link member 110, a mutual collision between the first link member 110 and the second link member 120 may be prevented.

However, the shape and the disposition of the first link member 110 and the second link member 120 are not limited thereto. The first link member 110 and the second link member 120 may be provided in any shape and disposition in which the first link member 110 and the second link member 120 may not mutually collide while being rotated in response to an operation of the drive portion 200.

The drive portion 200 may be disposed on the first link member 110 and the second link member 120 to rotate the first link member 110 and the second link member 120.

The drive portion 200 may include a first drive member 210 and a second drive member 220.

The first drive member 210 may be disposed at one end of the first link member 110. For example, the first link member 110 may be disposed in an upper portion of the first drive member 210.

Referring to FIG. 2, the first drive member 210 may rotate the first link member 110 on a first axis of rotation $X_1$. When a longitudinal central axis of the first drive member 210 matches the first axis of rotation $X_1$, the first link member 110 may rotate on the longitudinal central axis of the first drive member 210.

The second drive member 220 may be disposed at another end of the first link member 110.

When a connection element 112 is provided to compensate for a level difference between the first link member 110 and the second drive member 220, the second drive member 220 may be disposed on the connection element 112.

In this example, the connection element 112 and the second drive member 220 may be disposed on an identical axis, and the connection element 112 may be disposed to be in contact with an upper end of the second drive member 220.

The second drive member 220 may be disposed at one end of the second link member 120. For example, the second link member 120 may be disposed in a lower portion of the second drive member 220.

The second drive member 220 may rotate the second link member 120 on a second axis of rotation $X_2$. When a longitudinal central axis of the second drive member 220 matches the second axis of rotation $X_2$, the second link member 120 may rotate on the longitudinal central axis of the second drive member 220.

The first axis of rotation $X_1$ and the second axis of rotation $X_2$ may extend to be positioned at an identical point.

When the first axis of rotation $X_1$ is formed in a vertical direction, the second axis of rotation $X_2$ may be formed to tilt at a degrees (°) with respect to the first axis of rotation $X_1$. Thus, an angle between the first axis of rotation $X_1$ and the second axis of rotation $X_2$ may correspond to $\alpha°$.

The identical point at which the first axis of rotation $X_1$ and the second axis of rotation $X_2$, provided at both end portions of the first link member 110, are positioned may correspond to a central point O of the concentric spheres on which the first link member 110 and the second link member 120 are disposed.

When the emitting member 300, which will be described later, is disposed on the second link member 120, the emitting member 300 may be easily aimed at a target.

The drive portion 200 may have two degrees of freedom by means of the first drive member 210 and the second drive member 220, thereby spherically moving the emitting member 300. In this example, two motors may be used. Since a relatively few motors are used, an overall weight of the robot 10 may decrease.

The first link member 110 and the second link member 120 may rotate on the first axis of rotation $X_1$ and the second axis of rotation $X_2$ in different areas, respectively. Thus, an area accessed by the first link member 110 and the second link member 120 may be extended by the first drive member 210 and the second drive member 220, whereby a directivity of the link portion 100 with respect to a target may increase.

The emitting member 300 may be disposed at another end of the second link member 120.

Hereinafter, the emitting member 300 will be described based on a linear accelerator that emits radiation for radiation therapy.

However, the emitting member 300 is not limited thereto. The emitting member 300 may emit another material including a liquid or gas.

The second link member 120 may be disposed at a center of the emitting member 300. The emitting member 300 may be disposed to be perpendicular to a tangential direction of an end portion of the second link member 120.

Radiation or other materials may be emitted from a lower end of the emitting member 300. An angle at which radiation or other materials are emitted may be changed based on a tilting angle of the emitting member 300.

Referring to FIG. 2 again, the emitting member 300 may be disposed to tilt β° with respect to the second axis of rotation $X_2$, and disposed to tilt α°+β° with respect to the first axis of rotation $X_1$.

Angles α and β may be determined so that the first link member 110 and the second link member 120 may be smoothly rotated by the first drive member 210 and the second drive member 220 and the emitting member 300 may aim at a target over a relatively broader area.

A portion of the emitting member 300 at which radiation is emitted may be disposed on a third axis $X_3$. Thus, the radiation may be emitted from the emitting member 300 along the third axis $X_3$.

Similar to first axis of rotation $X_1$ and the second axis of rotation $X_2$, the third axis $X_3$ may also be positioned at the central point O of the concentric spheres.

That is, the first axis of rotation $X_1$, the second axis of rotation $X_2$, and the third axis $X_3$ may intersect at the central point O of the concentric spheres of the first link member 110 and the second link member 120.

Thus, a point at which radiation is to be emitted through the emitting member 300 may be adjusted by the link portion 100 and the drive portion 200.

Referring to FIG. 3, an angle adjustment element 310 may be additionally provided at an end portion of the second link member 120 or the emitting member 300.

The angle adjustment element 310 may be disposed at a point at which the emitting member 300 and the second link member 120 meet. The emitting member 300 may move in a direction of an arrow on the third axis $X_3$, and have a yaw movement.

As described above, the emitting member 300 including the angle adjustment element 310 may perform a small-angle movement. Thus, the angle adjustment element 310 may be useful when a minute angle adjustment is required after the emitting member 300 aims at a target by means of the drive portion 200.

The robot 10 may further include a controller (not shown). The first drive member 210 and the second drive member 220 may be easily controlled by the controller.

In detail, the controller may selectively or simultaneously operate the first drive member 210 or the second drive member 220 to dispose the emitting member 300 to face the target, and operate the angle adjustment element 310, as necessary.

The controller may control an operation of the first drive member 210 or the second drive member 220 to adjust a rotation velocity or a rotation direction of the first link member 110 or the second link member 120. Thus, a radiation surgery or treatment time may be reduced.

The robot 10 configured as described above according to an embodiment of the present invention may operate as follows. By operating the first drive member 210 or the second drive member 220, the first link member 110 or the second link member 120 may rotate.

The first link member 110 and the second link member 120 may be disposed on concentric spheres, and relatively rotate on different axes of rotation $X_1$, and $X_2$, respectively. Thus, the first link member 110 and the second link member 120 may smoothly rotate without a collision.

In addition, the first drive member 210 and the second drive member 220 may operate simultaneously or selectively. Thus, by operating the first drive member 210 and the second drive member 220 simultaneously, the first link member 110 and the second link member 120 may rotate simultaneously. Also, after the first link member 110 rotates by operating the first drive member 210, the second link member 120 may rotate by operating the second drive member 220.

In response to the rotation of the first link member 110 and the second link member 120, the emitting member 300 disposed at an end portion of the second link member 120 may move in a spherical pattern.

The angle adjustment element 310 may selectively operate.

The angle adjustment element 310 may minutely adjust an angle since the emitting member 300 may have a yaw movement on the third axis $X_3$.

Radiation may be emitted through the emitting member 300.

The radiation may be used to treat a target T, for example, an affected area of a patient.

Referring to FIG. 4, the emitting member 300 may emit radiation within an area A.

The area A may include an area in which the first link member 110 is rotated on the first axis of rotation $X_1$ by the first drive member 210, and an area in which the second link member 120 is rotated on the second axis of rotation $X_2$ by the second drive member 220.

When the first drive member 210 and the second drive member 220 operate simultaneously, a position of the emitting member 300 may be freely adjusted within the area A.

By operating the first drive member 210 and the second drive member 220, the emitting member 300 may aim at the target T or the affected area to be treated, and radiation emitted from the emitting member 300 may be concentrated on the target T.

When the emitting member 300 is to be relocated during treatment, by controlling the first drive member 210, the second drive member 220, or the angle adjustment element 310 through the controller, the emitting member 300 may be relocated more rapidly and accurately. When minute adjustment is required after the emitting member 300 is relocated, the minute adjustment may be performed by controlling the angle adjustment element 310.

As described above, a robot 10 according to an embodiment of the present invention may reduce a treatment or surgery time by aiming at a target more rapidly and accurately, increase a directivity with respect to the target through easy control, and reduce an overall weight through a compact design. In addition, the robot 10 may prevent a mutual collision between link members 110 and 120 during an operation of a drive portion 200, and adjust an angle at which a material is emitted from an emitting member 300 or an angle at which the emitting member 300 faces the target through an additional angle adjustment element 310 disposed at an end portion of a second link member 120 or the emitting member 300.

Hereinafter, a kinematical analysis on a structure of the robot 10 will be described in detail. Forward kinematics of a robot arm may be expressed as follows.

$$x = f(\theta) \quad \text{[Equation 1]}$$

In the Equation 1, θ denotes a joint angle, and x denotes a location and direction of an end-effector. Coordinates of an emitting member may be estimated based on an angle at which link members are connected to each other.

In addition, when a Denavit-Hartenberg (D-H) convention is used, the kinematics of the robot may include four parameters, for example, a link length a of a line member, a link offset d, a link distortion α, and a joint angle θ. In this example, when a joint rotates around a z axis, transformation matrices may be expressed as follows.

$$
{}^{0}_{1}T = \begin{bmatrix} c\theta1 & -c\alpha1 s\theta1 & s\alpha1 s\theta1 & 0 \\ s\theta1 & c\alpha1 c\theta1 & -s\alpha1 c\theta1 & 0 \\ 0 & s\alpha1 & c\alpha1 & R \\ 0 & 0 & 0 & 1 \end{bmatrix}
$$
[Transformation Matrix 1]

$$
{}^{1}_{2}T = \begin{bmatrix} c\theta2 & -c\alpha2 s\theta2 & s\alpha2 s\theta2 & 0 \\ s\theta2 & c\alpha2 c\theta2 & -s\alpha2 c\theta2 & 0 \\ 0 & s\alpha2 & c\alpha2 & R \\ 0 & 0 & 0 & 1 \end{bmatrix}
$$
[Transformation Matrix 2]

In Transformation Matrices 1 and 2, s denotes sine, and c denotes cosine. Through the above transformation matrices, a transformation matrix may be derived as follows.

[Transformation Matrix 3]

$$
{}^{0}_{2}T = \begin{bmatrix} c\theta1 c\theta2 - c\alpha1 s\theta1 c\theta1 & s\alpha1 s\alpha2 s\theta1 - c\alpha2(c\alpha1 c\theta2 s\theta1 + c\theta1 s\theta2) & c\alpha2 s\alpha1 s\theta1 + s\alpha2(c\alpha1 c\theta2 s\theta1 + c\theta1 s\theta2) & 0 \\ c\theta2 s\theta1 + c\alpha1 c\theta1 s\theta2 & -c\theta1 s\alpha1 s\alpha2 + c\alpha2(c\alpha1 c\theta1 c\theta2 - s\theta1 s\theta2) & -c\theta1(c\alpha2 s\alpha1 + c\alpha1 c\theta2 s\alpha2) + s\alpha2 s\theta1 s\theta2 & 0 \\ s\alpha1 s\theta2 & c\alpha2 c\theta2 s\alpha1 + c\alpha1 s\alpha2 & c\alpha1 c\alpha2 - c\theta2 s\alpha1 s\alpha2 & R \\ 0 & 0 & 0 & 1 \end{bmatrix}
$$

The above transformation matrix may represent a case in which two link members are provided. A point to which relocation is to be performed by a translation, an offset, a scale, or a rotation on a three-dimensional (3D) coordinate system may be estimated using the transformation matrix.

In addition, a location and direction of the emitting member 300 or the end-effector may be expressed as follows.

$$
{}^{0}_{2}T = \begin{bmatrix} {}^{0}x_2 & {}^{0}y_2 & {}^{0}z_2 & {}^{0}p_2 \\ 0 & 0 & 0 & 1 \end{bmatrix}
$$
[Transformation Matrix 4]

$$
{}^{0}p_2 = \begin{bmatrix} 0 \\ 0 \\ R \end{bmatrix}
$$
[Transformation Matrix 5]

In this example, the location of the emitting member 300 or the end-effector may be constantly uniform.

Figure 5:
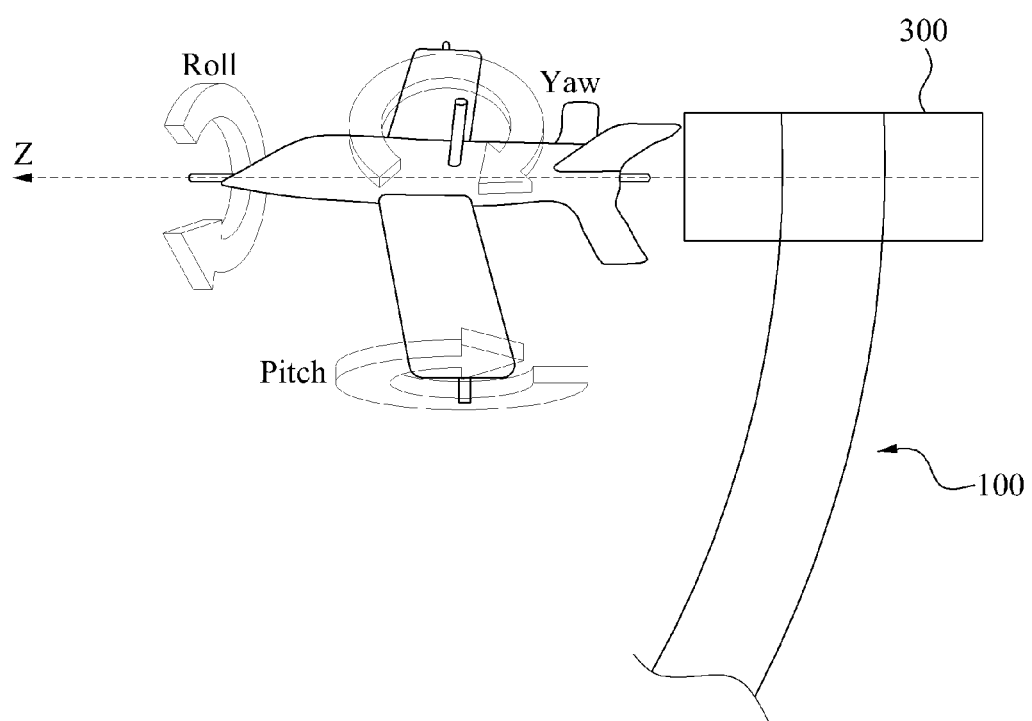
FIG. 5 illustrates a direction of an emitting member in a robot according to an embodiment of the present invention.

FIG. 5 illustrates a direction of the emitting member 300 in the robot 10. Referring to FIG. 5, the emitting member 300 may face a z axis, and have a roll movement of rotating on the z axis, a yaw movement of oscillating up and down based on the z axis, and a pitch movement of rotating up and down based on the z axis. In this example, a roll direction may be insignificant in the emitting member 300. Only a z-vector may be considered for a direction of the emitting member 300. Thus, Transformation Matrix 2 may be arranged as follows.

$$
{}^{0}z_2 = \begin{bmatrix} z_1 \\ z_2 \\ z_3 \end{bmatrix} =
$$
[Transformation Matrix 6]

$$
\begin{bmatrix} c\alpha2 s\alpha1 s\theta1 + s\alpha2(c\alpha1 c\theta2 s\theta1 + c\theta1 s\theta2) \\ -c\theta1(c\alpha2 s\alpha1 + c\alpha1\ c\theta2 s\alpha2) + s\alpha2 s\theta1 s\theta2 \\ c\alpha1 c\alpha2 - c\theta2 s\alpha1 s\alpha2 \end{bmatrix}
$$

Figure 6:
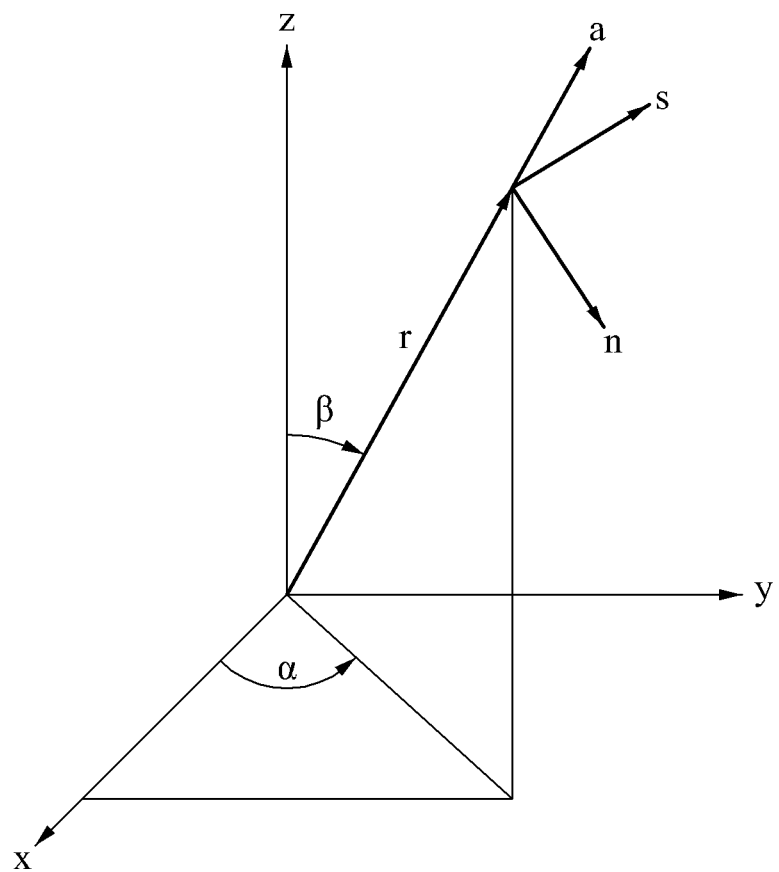
FIG. 6 illustrates spherical coordinates.

A desired direction of the emitting member 300 may be designated as spherical coordinates α and β of FIG. 6. When the direction of the emitting member 300 is given as a and β of FIG. 6, rotation matrices corresponding to the direction may be expressed as follows.

$$
R_{spherical} = R_{z,\alpha} R_{y,\beta} = \begin{bmatrix} c\alpha c\beta & -s\alpha & c\alpha s\beta \\ s\alpha c\beta & c\alpha & s\alpha s\beta \\ -s\beta & 0 & c\beta \end{bmatrix}
$$
[Rotation Matrix 1]

$$
R_{spherical} = \begin{bmatrix} x_1 & y_1 & z_1 \\ x_2 & y_2 & z_2 \\ x_3 & y_3 & z_3 \end{bmatrix}
$$
[Rotation Matrix 2]

Based on α and β from Rotation Matrices 1 and 2, ${}^{0}x_2 = [x_1, x_2, x_3]^T$, ${}^{0}y_2 = [y_1, y_2, y_3]^T$, and ${}^{0}z_2 = [z_1, z_2, z_3]^T$ may be determined, and $\theta_1$ and $\theta_2$ may also be determined. Such a relationship may be expressed by inverse kinematics as follows.

$$\theta = f(x)^{-1}$$
[Equation 2]

In Equation 2, x denotes a vector ${}^{0}z_2 = [z_1, z_2, z_3]^T$ and, θ denotes a vector including $\theta_1$ and $\theta_2$. Equation 2 may be an inverse function of Equation 1.

The joints angles $\theta_1$ and $\theta_2$ may be calculated based on orthonormal vectors ${}^{0}x_2$, ${}^{0}y_2$, and ${}^{0}z_2$. An intuitive method of calculating such vectors may be performed using spherical coordinates. When a direction is given as α and β, a rotation matrix corresponding to the direction may be expressed as follows.

$$
R_{spherical} = R_{z,\alpha} R_{y,\beta} = \begin{bmatrix} c\alpha c\beta & -s\alpha & c\alpha s\beta \\ s\alpha c\beta & c\alpha & s\alpha s\beta \\ -s\beta & 0 & c\beta \end{bmatrix}
$$
[Rotation Matrix 3]

In this example, constituent elements of the vectors may correspond to ${}^{0}x_2 = [x_1, x_2, x_3]^T$, ${}^{0}y_2 = [y_1, y_2, y_3]^T$, and ${}^{0}z_2 = [z_1, z_2, z_3]^T$.

The following Equations may be extracted from Transformation Matrix 3.

$$x_3 = s\alpha_1 s\theta_2$$

$$z_3 = c\alpha_1 c\alpha_2 - c\theta_2 s\alpha_1 s\alpha_2$$
[Equation 3]

In Equation 3, $\theta_2$ may be induced as follows.

$$s\theta_2 = x_3 - s\alpha_1$$
[Equation 4]

$$c\theta_2 = \frac{z_3 + c\alpha_1 c\alpha_2}{s\alpha_1 s\alpha_2}$$

$$\tan\theta_2 = \frac{s\alpha_1 s\alpha_2 (x_3 - s\alpha_1)}{z_3 + c\alpha_1 c\alpha_2}$$

$$\theta_2 = \arctan2\left(x_3 - s\alpha_1, \frac{z_3 + c\alpha_1 c\alpha_2}{s\alpha_1 s\alpha_2}\right)$$

A function arctan 2, an arctangent function including two input variables, may be used due to a stability of being close to zero input values and a characteristic of a final angle returning to an appropriate quadrant. $\theta_1$ may be calculated as follows. The following Equations 5 through 7 may be obtained from Transformation Matrix 4.

$$(x_2 = c\theta_2 s\theta_1 + c\alpha_1 c\theta_1 s\theta_2)c\alpha_1 s\theta_2$$ [Equation 5]
$$(x_1 = -s\theta_1 c\alpha_1 s\theta_2 + c\theta_1 c\theta_2)c\theta_2$$

$$c\alpha_1 s\theta_2 x_2 + c\theta_2 x_1 = c^2\alpha_1 s^2\theta_2 c\theta_1 + c^2\theta_2 c\theta_1$$ [Equation 6]
$$c\theta_1 = \frac{c\alpha_1 s\theta_2 x_2 + c\theta_2 x_1}{c_1^2 s^2\theta_2 + c^2\theta_2}$$

$$z_1 = (c\alpha_2 s\alpha_1 + s\alpha_2 c\alpha_1 c\theta_2)s\theta_1 + s\alpha_2 s\theta_2 c\theta_1$$ [Equation 7]
$$z_2 = -(c\alpha_2 s\alpha_1 + s\alpha_2 c\alpha_1 c\theta_2)c\theta_1 + s\alpha_2 s\theta_2 s\theta_1$$

In addition, the following may be assumed.

$$a = c\alpha_2 s\alpha_1 + s\alpha_2 c\alpha_1$$

$$b = s\alpha_2 s\theta_2$$ [Equation 8]

Through Equations 7 and 8, the following may be calculated.

$$a(z_1 = as\theta_1 + bc\theta_1)$$ [Equation 9]
$$b(z_2 = -ac\theta_1 + bs\theta_1)$$
$$az_1 = a^2 s\theta_1 + abc\theta_1$$
$$bz_2 = b^2 s\theta_1 - abc\theta_1$$
$$az_1 + bz_2 = (a^2 + b^2)s\theta_1$$
$$s\theta_1 = \frac{az_2 + bz_2}{a^2 + b^2}$$

Through Equations 6 and 9, $\theta_1$ may be calculated as follows.

$$\theta_1 = \arctan2\left(\frac{az_1 + bz_2}{a^2 + b^2}, \frac{c\alpha_1 s\theta_2 x_2 + c\theta_2 x_1}{c^2\alpha_1 s^2\theta_2 + c^2\theta_2}\right)$$ [Equation 10]

From Equations 4 and 10, the two joint angles $\theta_1$ and $\theta_2$ may be determined. A Jacobian matrix will be described hereinafter. A linear mapping between a $\theta$-space and an x-space may be as follows. Equation 1 may be differentiated as follows.

$$^0\dot{x} = {}^0 J \dot{\theta}$$ [Jacobian Matrix 1]

$$^0 J = \begin{bmatrix} {}^0z_0 \times ({}^0p_n - {}^0p_0) & {}^0z_1 \times ({}^0p_n - {}^0p_1) \\ {}^0z_0 & {}^0z_1 \end{bmatrix}$$

The Transformation Matrix 1 may be expressed as follows.

$$^0_1 T = \begin{bmatrix} {}^0x_1 & {}^0y_1 & {}^0z_1 & {}^0p_1 \\ 0 & 0 & 0 & 1 \end{bmatrix} =$$ [Rotation Matrix 7]

$$\begin{bmatrix} c\theta 1 & -c\alpha 1 s\theta 1 & s\alpha 1 s\theta 1 & 0 \\ s\theta 1 & c\alpha 1 c\theta 1 & -s\alpha 1 c\theta 1 & 0 \\ 0 & s\alpha 1 & c\alpha 1 & R \\ 0 & 0 & 0 & 1 \end{bmatrix}$$

Thus, the Jacobian matrix may be expressed as follows.

[Jacobian Matrix 2]

$$^0 J = \begin{bmatrix} \begin{bmatrix} 0 \\ 0 \\ 1 \end{bmatrix} \times \left(\begin{bmatrix} 0 \\ 0 \\ R \end{bmatrix} - \begin{bmatrix} 0 \\ 0 \\ 0 \end{bmatrix}\right) & \begin{bmatrix} s\alpha 1 s\theta 1 \\ -s\alpha 1 c\theta 1 \\ c\alpha 1 \end{bmatrix} \times \left(\begin{bmatrix} 0 \\ 0 \\ R \end{bmatrix} - \begin{bmatrix} 0 \\ 0 \\ R \end{bmatrix}\right) \\ \begin{bmatrix} 0 \\ 0 \\ 1 \end{bmatrix} & \begin{bmatrix} s\alpha 1 s\theta 1 \\ -s\alpha 1 c\theta 1 \\ c\alpha 1 \end{bmatrix} \end{bmatrix}$$

[Jacobian Matrix 3]

$$^0 J = \begin{bmatrix} {}^0z_0 \times ({}^0p_n - {}^0p_0) & {}^0z_1 \times ({}^0p_n - {}^0p_1) \\ {}^0z_0 & {}^0z_1 \end{bmatrix}$$

$$= \begin{bmatrix} \begin{bmatrix} 0 \\ 0 \\ 1 \end{bmatrix} \times \left(\begin{bmatrix} 0 \\ 0 \\ R \end{bmatrix} - \begin{bmatrix} 0 \\ 0 \\ 0 \end{bmatrix}\right) & \begin{bmatrix} s\alpha 1 s\theta 1 \\ -s\alpha 1 c\theta 1 \\ c\alpha 1 \end{bmatrix} \times \left(\begin{bmatrix} 0 \\ 0 \\ R \end{bmatrix} - \begin{bmatrix} 0 \\ 0 \\ R \end{bmatrix}\right) \\ \begin{bmatrix} 0 \\ 0 \\ 1 \end{bmatrix} & \begin{bmatrix} s\alpha 1 s\theta 1 \\ -s\alpha 1 c\theta 1 \\ c\alpha 1 \end{bmatrix} \end{bmatrix}$$

$$= \begin{bmatrix} \begin{bmatrix} 0 \\ 0 \\ 0 \end{bmatrix} & \begin{bmatrix} 0 \\ 0 \\ 0 \end{bmatrix} \\ \begin{bmatrix} 0 \\ 0 \\ 1 \end{bmatrix} & \begin{bmatrix} s\alpha 1 s\theta 1 \\ -s\alpha 1 c\theta 1 \\ c\alpha 1 \end{bmatrix} \end{bmatrix}$$

Thus, the Jacobian matrix may be expressed as follows.

$$J = \begin{bmatrix} 0 & s\alpha 1 s\theta 1 \\ 0 & -s\alpha 1 c\theta 1 \\ 1 & c\alpha 1 \end{bmatrix}$$ [Jacobian Matrix 4]

Through Jacobian Matrix 4, when only an angular velocity is considered and a translational velocity is not considered, a singularity may not be achieved except for a case in which $\alpha = n\pi$ and $n \in N$ are satisfied.

As described above, a relationship between a joint velocity of a link member and a velocity of an emitting member may be determined through a Jacobian matrix. Thus, a moving velocity of the emitting member may be estimated based on the joint velocity of the link member. In addition, when a desired velocity of the emitting member is given, a joint velocity of the link member that may achieve the desired velocity of the emitting member may be inversely calculated.

In detail, a location of the emitting member may be estimated based on a current location of a link member. Conversely, to enable the emitting member to face a central point or a target, an operation of a link member may be controlled based on a current location of the emitting member.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A robot comprising:
a link portion comprising a plurality of link members; and
a drive portion to rotate the plurality of link members,
wherein axes of rotation of the drive portion extending from end portions of the plurality of link members are positioned at an identical point;
wherein the plurality of link members comprise:
a first link member; and
a second link member connected to an end portion of the first link member; and
wherein the first link member and the second link member are provided in a form of arcs and disposed on concentric spheres, respectively.

2. The robot of claim 1, wherein the axes of rotation of the drive portion are positioned at a center of the concentric spheres.

3. The robot of claim 1, wherein the first link member and the second link member are disposed away from a location at which the first link member and the second link member are radially spaced with respect to each other.

4. The robot of claim 1, wherein the first link member and the second link member are provided in different lengths, and between the first link member and the second link member, an externally disposed link member is provided to have a greater length than an internally disposed link member.

5. The robot of claim 1, wherein the drive portion comprises:
a first drive member disposed at one end of the first link member to rotate the first link member on a first axis of rotation; and
a second drive member disposed at another end of the first link member to rotate the second link member on a second axis of rotation.

6. The robot of claim 5, wherein the first axis of rotation and the second axis of rotation are positioned at the identical point, and a length of the first link member is determined based on an angle between the first axis of rotation and the second axis of rotation.

7. The robot of claim 5, wherein the first axis of rotation is perpendicular to a tangential direction of the one end of the first link member, and the second axis of rotation is perpendicular to a tangential direction of the another end of the first link member.

8. The robot of claim 1, and further comprising an emitting member disposed at another end of the second link member to face a target, and wherein the emitting member comprises a linear accelerator to emit radiation for radiation therapy.

9. The robot of claim 8, wherein the emitting member is disposed to be perpendicular to a tangential direction of an end portion of the second link member.

10. The robot of claim 8, wherein the emitting member is moved spherically around the target along a trajectory of rotation of the second link member.

11. The robot of claim 8, and further comprising an angle adjustment element disposed at the second link member or the emitting member to adjust an angle at which the emitting member faces the target.

12. A robot comprising:
a first link member;
a first drive member disposed at one end of the first link member to rotate the first link member on a first axis of rotation;
a second link member connected to another end of the first link member;
a second drive member disposed between the another end of the first link member and one end of the second link member to rotate the second link member on a second axis of rotation; and
an emitting member disposed at another end of the second link member,
wherein the first axis of rotation and the second axis of rotation are positioned at an identical location of a target,
wherein the first link member and the second link member are provided in a form of arcs and disposed on concentric spheres on which the target is centered, respectively.

13. The robot of claim 12, wherein a length of the first link member is determined based on an angle between the first axis of rotation and the second axis of rotation.

14. The robot of claim 12, wherein the first axis of rotation is perpendicular to a tangential direction of the one end of the first link member, and the second axis of rotation is perpendicular to a tangential direction of the one end of the second link member.

15. The robot of claim 12, wherein a third axis is formed in a direction extending from the emitting member to the target, and a length of the second link member is determined based on an angle between the second axis of rotation and the third axis.

16. The robot of claim 12, and further comprising an angle adjustment element disposed at the second link member or the emitting member to adjust an angle at which the emitting member faces the target.

17. A robot comprising:
a first link member;
a first drive member disposed at one end of the first link member to rotate the first link member on a first axis of rotation;
a second link member connected to another end of the first link member;
a second drive member disposed between the another of the first link member and one end of the second link member to rotate the second link member on a second axis of rotation; and
an emitting member disposed at another end of the second link member;
wherein the first axis of rotation and the second axis of rotation are positioned at an identical location of a target; and
wherein the first link member and the second link member are disposed away from a location at which the first link member and the second link member are radially spaced with respect to each other.

* * * * *